United States Patent [19]
Dujardin et al.

[11] Patent Number: 4,873,376
[45] Date of Patent: Oct. 10, 1989

[54] PROCESS FOR THE PRODUCTION OF MONOMERIC ALKENYLPHENOLS FROM DIHYDROXYDIPHENYLALKANES

[75] Inventors: Ralf Dujardin; Wolfgang Ebert, both of Krefeld, Fed. Rep. of Germany

[73] Assignee: Bayer Aktiengesellschaft, Leverkusen Bayerwerk, Fed. Rep. of Germany

[21] Appl. No.: 209,200

[22] Filed: Jun. 20, 1988

[30] Foreign Application Priority Data

Jul. 2, 1987 [DE] Fed. Rep. of Germany ....... 3721853

[51] Int. Cl.$^4$ .................. C07C 37/52; C07C 37/50
[52] U.S. Cl. .................................. 568/806; 568/781; 568/782
[58] Field of Search .................. 568/781, 782, 806

[56] References Cited

U.S. PATENT DOCUMENTS

| 4,242,528 | 12/1980 | Kato et al. | 568/781 |
| 4,245,128 | 1/1981 | Kato et al. | 568/806 |
| 4,594,459 | 6/1986 | Inoue | 568/781 |
| 4,657,890 | 4/1987 | Gares et al. | 502/340 |

FOREIGN PATENT DOCUMENTS

| 1235894 | 3/1967 | Fed. Rep. of Germany | 568/806 |
| 2932954 | 2/1980 | Fed. Rep. of Germany | 568/806 |
| 2932959 | 2/1980 | Fed. Rep. of Germany | 568/781 |

OTHER PUBLICATIONS

Patent Abstracts of Japan, Unexamined Applications, C Field, vol. 4, No. 85, 1980.

Primary Examiner—Werren B. Lone
Attorney, Agent, or Firm—Connolly and Hutz

[57] ABSTRACT

The invention relates to a process for the production of monomeric alkenylphenols from dihydroxydiphenylalkanes by thermal cleavage in certain solvents.

6 Claims, No Drawings

PROCESS FOR THE PRODUCTION OF MONOMERIC ALKENYLPHENOLS FROM DIHYDROXYDIPHENYLALKANES

This invention relates to a process for the production of monomeric alkenylphenols from dihydroxydiphenylalkanes by thermal cleavage in certain solvents.

It is known that dihydroxydiphenylalkanes can be thermally cleaved in the presence of a basic catalyst to phenol and alkenylphenol.

It is known from GB-PS No. 905,994 that dihydroxydiphenylpropane can be cleaved with alkali under reduced pressure in the melt, the cleavage product distilling off. In this process, dihydroxydiphenylpropane is evaporated in an evaporator of the liquid film type at 260° C. The vapor is then passed over a catalyst bed of soda lime to be decomposed in the gas phase.

Other known processes use a reaction medium which is involatile and inert under the cleavage conditions. For example, DE-OS No. 29 32 954 describes a process for the base-catalyzed cleavage of dihydroxydiphenylalkanes in which continuously melted dihydroxydiphenylalkane is introduced at elevated temperature into a reaction medium which contains the basic catalyst and from which the alkenylphenols split off are then continuously distilled off under reduced pressure.

One disadvantage attending the known methods is that, in addition to the monomeric alkenylphenols, the cleavage product obtained mainly contains dimeric alkylphenol and phenol (for example DE-OS No. 29 32 954). As a result, involved purification processes, for example distillations or recrystallizations, are required for separating off the phenol (for example DE-PS No. 1 253 894). The crude mixture, which consists mainly of dimeric alkenylphenol, then has to be thermally cleaved again to obtain pure monomeric alkenylphenol.

This complicated, cost-intensive and time-consuming purification process also reduces the yield of monomeric alkenylphenol.

It has now been found that alkenylphenols can be obtained more easily in better yields by cleavage of alkylidene bisphenols providing the cleavage is carried out in the presence of special solvents.

Accordingly, the present invention relates to a process for the production of monomeric alkenylphenols from dihydroxydiphenylalkanes in the presence of basic catalysts, characterized in that a solution of dihydroxydiphenylalkane and a water-miscible organic solvent is continuously introduced into an organic reaction medium containing the basic catalyst under reduced pressure and at elevated temperature at such a rate that the initial volume of the reaction medium is increased by up to 10% by volume and the cleavage products are continuously distilled off together with the solvent from the reaction system into a water-filled receiver from which the monomeric alkenylphenol is isolated and the phenol formed as secondary product and the solvent remain dissolved in the aqueous phase.

Geminal dihydroxydiphenylalkanes, preferably nucleusunsubstituted dihydroxydiphenyl derivatives of aliphatic or alicyclic hydrocarbons, which may be cleaved into an alkenylphenol and phenol, are used in the process according to the invention.

The dihydroxydiphenylalkanes used in accordance with the invention correspond to the following general formula

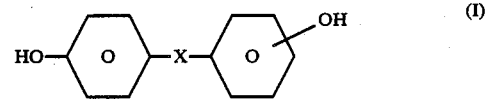

in which X is a geminal $C_2$–$C_{12}$ *alkylidene radical, a geminal* $C_5$–$C_7$ cycloalkylidene radical or a geminal $C_8$–$C_{12}$ aralkylidene radical.

Examples of dihydroxydiphenylalkanes of formula (I) suitable for use in accordance with the invention are 2,2-(4,4'-dihydroxydiphenyl)-propane, 2-(4-hydroxyphenyl) -2-(2'-hydroxyphenyl)-propane, 1,1-(4,4'-dihydroxydiphenyl)-ethane, 1,1-(4,4'-dihydroxydiphenyl)-propane, 1,1-(4,4'-dihydroxydiphenyl)-butane, 2,2-(4,4'-dihydroxydiphenyl)-butane, 2,2-(4,4'-dihydroxydiphenyl)-3-methylbutane, 1,1-(4,4'-dihydroxydiphenyl)-2-methylpropane, 2,2-(4,4'-dihydroxydiphenyl)-pentane, 3,3-(4,4'-dihydroxydiphenyl)-pentane, 2,2-(4,4'-dihydroxydiphenyl)-4-methylpentane, 4,4-(4,4'-dihydroxydiphenyl)-heptane, 1,1-(4,4'-dihydroxydiphenyl)-cyclohexane, 1,1-(4,4'-dihydroxydiphenyl)-1-phenylethane, etc. 2,2-(4,4'-Dihydroxydiphenyl)-propane is preferred.

According to the invention, not only pure dihydroxydiphenylalkanes, but also crude products, for example of the type obtained in the commercial production of the dihydroxydiphenylalkanes from phenols and ketones, may be used as starting material. The process according to the invention is carried out at a temperature of 150° to 250° C. Temperatures of 200° to 240° C. are preferred.

In the process according to the invention, the cleavage product is rapidly distilled off from the reaction system under a pressure of 1,000 to 15,000 Pa.

Inert, high-boiling organic solvents are used for carrying out the process according to the invention. Their boiling point under normal pressure is up to 350° C. They should advantageously dissolve the dihydroxydiphenylalkanes at temperatures below 150° C. The solvents (diluents) are preferably miscible with water.

Examples of organic solvents are oligomeric 1,2-$C_2$–$C_4$-alkylidene glycols, such as diethylene glycol, dipropylene glycol, triethylene glycol and tripropylene glycol; di- and trialkanolamines, for example diethanolamine, diisopropanolamine, triethanolamine and triisopropanolamine; N-alkyl lactams, for example N-methyl pyrrolidone and N-methyl-ε-caprolactam, etc. Diethylene glycol and triethylene glycol are preferred.

Basic catalysts are used in the process according to the invention. Examples of suitable basic catalysts are oxides, hydroxides or carbonates of alkali metals or alkaline earth metals, such as sodium hydroxide, potassium hydroxide, sodium carbonate, potassium carbonate, calcium oxide and calcium hydroxide; alkali metal salts of phenols, such as sodium phenolate or a sodium salt of a condensate formed from phenol or cresol and acetone (for example bisphenol A) and alkali metal salts of mildly acidic fatty acids, such as sodium acetate, etc. The basic catalyst is used in a quantity of 0.01 to 5% by weight, based on the weight of the solvent used.

To carry out the cleavage reaction according to the invention, in which the reaction medium (solvent) and the basic catalyst are introduced into a reactor which is equipped with a charging inlet for a starting material, a distillation outlet for the cleavage products, a thermometer and optionally a stirrer (or mixer), the reaction medium containing the basic catalyst is initially introduced at elevated temperature under a reduced pressure of 1,000 to 15,000 Pa and the dihydroxydiphenylalkane dissolved in the solvent is subsequently added.

The dihydroxydiphenylalkane is then cleaved into alkenylphenol and phenol, the cleavage products being evaporated with part of the solvent. This vapor is rapidly distilled off from the reaction system into a receiver filled with cold water (5°–40° C.). The cleavage products separate into two phases, one of which contains the monomeric alkenylphenol and, optionally, small quantities of phenol while the other phase, the aqueous phase, contains the phenol formed and the solvent used.

The alkenylphenols may accumulate in finely crystalline form or in liquid form. Solid alkenylphenols may readily be separated off by filtration while liquid alkenylphenols may readily be separated off by phase separation.

Where the alkenylphenol still contains phenol, it is purified by known methods.

According to the invention, the quantity of water in the receiver amounts to between 1 and 3 times the quantity by weight of dihydroxydiphenylalkane solution used, depending on the alkenylphenol being produced.

The process according to the invention, including isolation of the monomeric alkenylphenols, may be carried out continuously and discontinuously.

In the process according to the invention, the dihydroxydiphenylalkane solution is continuously added to the reaction medium in such a way that the volume of the reaction medium increases by up to 10%. The increase in volume of the reaction medium is preferably kept in the range from 2 to 5% by volume.

The reaction according to the invention is carried out with mixing, preferably stirring, including the water in the receiver.

The process according to the invention is preferably carried out in an inert gas, such as nitrogen, helium or argon.

According to the invention, the monomeric alkenylphenols are obtained in highly pure form and in very good yields. In most cases, further purification is not absolutely necessary.

In the following Examples, percentages are percentages by weight.

EXAMPLE 1

A reactor (1 liter) equipped with a thermometer, a charging inlet for the starting material and a distillation inlet for the cleavage products was charged with 250 g triethylene glycol and 1 g sodium hydroxide, after which nitrogen was passed through the reaction medium for 10 minutes. The temperature of the triethylene glycol was kept at 230° C. and the interior of the reactor under a pressure of 2666 Pa. A hot solution (100° C.) of 500 g 2,2-di-(4,4-hydroxyphenyl)propane (hereinafter referred to as bisphenol A) and 450 g triethylene glycol was continuously introduced into the heated triethylene glycol through the charging inlet at a rate of 475 g/h. The mixture of triethylene glycol, p-isopropenyl phenol and phenol distilling off from the reactor was collected with stirring in the receiver (capacity 3 l) filled with 1.5 liters cold water (20°), the p-isopropenyl phenol precipitating as a white finely crystalline deposit which was subsequently isolated by filtration.

After drying, the reaction produced 279 g monomeric p-isopropenyl phenol having a purity of greater than 99% (as determined by H-NMR) from 500 g bisphenol A in 2 hours.

EXAMPLE 2

The same reactor as in Example 1 was charged with 100 g triethanolamine and 1 g sodium hydroxide. A solution of 500 g bisphenol A and 500 g triethanolamine was split off under the same conditions as in Example 1. 279 g monomeric p-isopropenyl phenol having a purity of 99% were obtained from 500 g bisphenol A in 8 hours.

EXAMPLE 3

The same reactor as in Example 1 was charged with 100 g triethylene glycol and 0.1 g sodium hydroxide and nitrogen subsequently passed through the reaction medium for 10 minutes. A solution of 1,000 g 1,1-bis-(4-hydroxyphenyl)cyclohexane (hereinafter referred to as bisphenol Z) and 1,150 g triethylene glycol was continuously introduced into the heated triethylene glycol through the charging inlet at a rate of 500 g/h.

1-(4-hydroxyphenyl)-1-cyclohexene was isolated in the same way as described in Example 1 for the p-isopropenyl phenol. 641 g monomeric 1-(4-hydroxyphenyl)-1-cyclohexene having a purity of 99% were obtained from 1,000 g bisphenol Z.

We claim:

1. A process for the production of monomeric alkenylphenols from dihydroxydiphenylalkanes in the presence of basic catalysts which comprise oxides, hydroxides or carbonates of alkali metals or alkaline earth metals, alkali metal salts of phenols or alkali metal salts of mildly acidic fatty acids, wherein a solution of dihydroxydiphenylalkane and a water-miscible organic solvent, which is oligomeric 1,2-($C_2$–$C_4$)- alkylidene glycols, di- and trialkanolamines or N-alkyl lactams, is continuously introduced into an organic reaction medium containing the basic catalyst under reduced pressure and at elevated temperature of from 150° to 250° C. at such a rate that the initial volume of the reaction medium increases by up to 10% by volume and the cleavage products are continuously distilled off together with the solvent from the reaction system into a water-filled receiver from which the monomeric alkenylphenol is then isolated and the phenol formed as secondary product and the solvent remain dissolved in the aqueous phase.

2. A process as claimed in claim 1, characterized in that 2,2-bis(4-hydroxyphenyl)-propane is used as the dihydroxydiphenylalkane.

3. A process as claimed in claim 1, characterized in that the process is carried out in an inert gas.

4. A process as claimed in claim 1 wherein the solvent is diethylene glycol or triethylene glycol.

5. A process as claimed in claim 1 wherein the temperature is 200° to 240° C.

6. A process as claimed in claim 1 wherein the catalyst is sodium hydroxide.

* * * * *